US008085899B2

(12) United States Patent
Nord et al.

(10) Patent No.: US 8,085,899 B2
(45) Date of Patent: Dec. 27, 2011

(54) TREATMENT PLANNING SYSTEM AND METHOD FOR RADIOTHERAPY

(75) Inventors: Janne Ilmari Nord, Espoo (FI); Marko Tapio Rusanen, Helsinki (FI)

(73) Assignee: Varian Medical Systems International AG, Zug (CH)

( * ) Notice: Subject to any disclaimer, the term of this patent is extended or adjusted under 35 U.S.C. 154(b) by 494 days.

(21) Appl. No.: 11/954,638

(22) Filed: Dec. 12, 2007

(65) Prior Publication Data
US 2009/0154644 A1 Jun. 18, 2009

(51) Int. Cl.
*A61N 5/10* (2006.01)
(52) U.S. Cl. .......................................................... 378/65
(58) Field of Classification Search ...................... 378/65
See application file for complete search history.

(56) References Cited

U.S. PATENT DOCUMENTS

| | | | |
|---|---|---|---|
| 5,602,892 A | 2/1997 | Llacer | |
| 5,782,739 A | 7/1998 | Criss et al. | |
| 6,038,283 A | 3/2000 | Carol et al. | |
| 6,260,005 B1 | 7/2001 | Yang et al. | |
| 6,393,096 B1 * | 5/2002 | Carol et al. | 378/65 |
| 6,411,675 B1 | 6/2002 | Llacer | |
| 6,560,311 B1 | 5/2003 | Shepard et al. | |
| 6,661,870 B2 | 12/2003 | Kapatoes et al. | |
| 6,661,872 B2 * | 12/2003 | Bova | 378/65 |
| 6,735,277 B2 * | 5/2004 | McNutt et al. | 378/65 |
| 6,879,659 B2 * | 4/2005 | Alber | 378/65 |
| 6,882,702 B2 | 4/2005 | Luo | |
| 7,162,008 B2 * | 1/2007 | Earl et al. | 378/65 |
| 7,180,980 B2 * | 2/2007 | Nguyen | 378/65 |

(Continued)

FOREIGN PATENT DOCUMENTS
WO   WO 2005/035061 A2   4/2005

OTHER PUBLICATIONS

Siebers, Jeffrey V. et al., "Acceleration of Dose Calculations for Intensity-Modulated Radiotherapy", *Medical Physics*, Jun. 2001, pp. 903-910, vol. 28: 6, American Association of Physicists in Medicine, US, 8 page(s).
Xing, L. et al., "Fast Iterative Algorithms for Three-Dimensional Inverse Treatment Planning", *Medical Physics*, Oct. 1998, pp. 1845-1849, vol. 25: 10, American Association of Physicists in Medicine, US, 5 page(s).

(Continued)

*Primary Examiner* — Irakli Kiknadze
*Assistant Examiner* — Thomas R Artman
(74) *Attorney, Agent, or Firm* — Kilpatrick Townsend & Stockton LLP

(57) ABSTRACT

A treatment planning method and system for optimizing a treatment plan used to irradiate a treatment volume including a target volume, such as a tumor, is disclosed. According to the method, two dose calculation algorithms are used to develop the optimized treatment plan. A first dose calculation algorithm is used to obtain substantially complete dose calculations and a second, incremental, dose calculation algorithm is used to make more limited calculations. The incremental calculations may be performed, for example, with less precision, less accuracy or less scope (e.g., focused on a specific subvolume within the treatment volume) in order to reduce the time required to achieve an optimized plan. Each of the dose calculation algorithms may be iterated a plurality of times, and different cutoff criteria can be used to limit the number of iterations in a given pass. A treatment planning system of the invention uses software for implementing the complete and incremental dose calculation algorithms. The method and system are especially useful for IMRT and arc therapy where treatment plan optimization is particularly challenging.

20 Claims, 4 Drawing Sheets

U.S. PATENT DOCUMENTS

| | | | |
|---|---|---|---|
| 7,333,591 B2 * | 2/2008 | Earl et al. | 378/65 |
| 2003/0048868 A1 | 3/2003 | Bailey et al. | |
| 2005/0111621 A1 * | 5/2005 | Riker et al. | 378/65 |
| 2006/0045238 A1 * | 3/2006 | Nguyen | 378/65 |
| 2007/0064871 A1 * | 3/2007 | Earl et al. | 378/65 |

OTHER PUBLICATIONS

Djajaputra, David et al.; "Algorithm and performance of a clinical IMRT beam-angle optimization system"; 2003, *Phy. Med. Bio.*, vol. 48, pp. 3191-3212.

\* cited by examiner

TREATMENT PLANNING SYSTEM AND METHOD FOR RADIOTHERAPY

The present invention relates generally to treatment planning for radiotherapy and is more particularly directed to systems and methods for calculating and optimizing a treatment plan.

BACKGROUND OF THE INVENTION

Modern radiation therapy techniques include the use of Intensity Modulated Radiotherapy ("IMRT"), typically by means of a radiotherapy system, such as a linear accelerator, equipped with a multileaf collimator ("MLC"). Use of multileaf collimators in general, and IMRT in particular, allows the radiologist to treat a patient from multiple angles while varying the shape and dose of the radiation beam, thereby providing greatly enhanced ability to deliver radiation to a target within a treatment volume while avoiding excess irradiation of nearby healthy tissue. However, the greater freedom which IMRT and other complex radiotherapy techniques, such as volumetric modulated arc therapy (where the system gantry moves while radiation is delivered) and three-dimensional conformal radiotherapy ("3D conformal" or "3DCRT"), afford to radiologists has made the task of developing treatment plans more difficult. As used herein, the term radiotherapy should be broadly construed and is intended to include various techniques used to irradiate a patient, including use of photons (such as high energy x-rays and gamma rays), particles (such as electron and proton beams), and radiosurgical techniques. While modern linear accelerators use MLCs, other methods of providing conformal radiation to a target volume are known and are within the scope of the present invention.

Treatment planning starts typically with (1) images of the treatment volume (e.g., slices from CT or MRI scans) and, (2) the desired dose of radiation which is to be delivered to a target, such as a tumor, within the treatment volume, and (3) the maximum dose which can be safely absorbed by tissue structures, such as organs, within the treatment volume that are adjacent to or near the tumor or other target volume. As used herein, the term "treatment volume" is used to refer to the entire volume that will be subjected to radiation, and is sometimes referred to as the "irradiated volume." The target volume, intended to receive a therapeutic prescribed dose, is sometimes referred to as the "planning target volume" ("PTV"). Both the target within the treatment volume and any nearby organs may have complex three dimensional shapes adding to the difficulty of preparing a treatment plan.

A variety of algorithms have been developed to solve the "inverse problem" of devising and optimizing a specific, three-dimensional treatment plan for irradiating the treatment volume from a variety of angles or, in arc therapy, while the system gantry is moving, to deliver a desired radiation dose to the target while minimizing irradiation of nearby tissue, taking into account the capabilities and physical limitations of the radiotherapy system. Generally speaking, the inverse problem involves optimizing the angles, MLC leaf movements and durations of irradiations. Because of the large number of variables involved and complex matrix manipulations that are required, the algorithms for calculating and optimizing treatment plans require substantial computational time even when using modern high speed computers.

Generally two types of algorithms are used in treatment planning: (1) dose calculations algorithms based on a given set system parameters, e.g., gantry angle, MLC leaf positions, etc., and (2) search algorithms which use various techniques to adjust system parameters between dose calculations to achieve optimization of the plan. Known dose calculation algorithms include various Monte Carlo ("MC") techniques, pencil beam convolution ("PBC"), generalized Gaussian pencil beam ("GGPB"), collapsed cone convolution ("CCC"), and anisotropic analytical algorithm ("AAA"). Known search algorithms include various stochastic and deterministic methods, including various simulated annealing ("SA") techniques, algebraic inverse treatment planning ("AITP"), simultaneous iterative inverse treatment planning ("SIITP"), iterative least-square inverse treatment planning ("ILSITP"), and superposition convolution ("SC"). Such techniques are well known in the art, and each of the techniques has advantages and disadvantages relative to the others. For example, stochastic dose calculation methods such as Monte Carlo are more accurate, but typically require more time to perform. Each of the methods requires iterative dose calculations for optimization, and generally a high number of dose calculation iterations or "passes" are required to converge on an optimal plan. Typically, each iteration involves changing the boundary conditions using the search algorithm and recalculating the dose distribution. While a fully optimized plan might be achieved using known methods if adequate time is available, as a practical matter time constraints often limit the ability to achieve this goal.

It is noted that a treatment plan is typically implemented over a time period. Thus, the patient typically is given multiple treatments over the course of days or weeks, such that the dose delivered to the treatment volume is fractionated. During the time between treatments changes may occur in the treatment volume, for example, the tumor being irradiated may shrink in size or surrounding organs may change position. Any such changes may necessitate revising and re-optimizing the treatment plan before the next fractionated dose is delivered. The problem of re-optimizing a treatment plan is known, and presents somewhat different issues than achieving an initially optimized plan as described herein.

Treatment planning algorithms may be implemented as part of an overall, integrated treatment planning software package which provides additional features and capabilities. For example, a dose calculation algorithm and search algorithm may be used to optimize a set of fluence maps at each gantry angle, with a separate leaf sequencer used to calculate the leaf movements needed to deliver them. Alternatively, a dose calculation algorithm and search algorithm may be used to directly optimize leaf movements and other machine parameters. The Eclipse™ Treatment Planning System offered by the assignee of the present invention includes such an integrated software program.

Accordingly, there is a need for improved systems and methods to efficiently perform dose calculation to optimize a radiotherapy treatment plan.

SUMMARY OF THE INVENTION

The present invention is directed to a method and system for optimizing a treatment plan for irradiating a treatment volume which includes a target volume. In accordance with the present invention, at least two dose calculation algorithms are used to optimize the treatment plan. Specifically, the method and system of preferred embodiments of the present invention use a first algorithm to perform substantially complete dose calculations and a second algorithm to perform incremental dose calculations.

The first general embodiment of the present invention, comprises a method of optimizing a treatment plan for irradiating a treatment volume within a patient from a plurality of angles, including the steps of: making a substantially complete dose calculation using a first dose calculation algorithm, and thereafter, making at least one incremental dose calculation using a second dose calculation algorithm that is different from the first dose calculation algorithm. A substantially complete dose calculation can be performed after making an incremental dose calculation using a third dose calculation algorithm that is different from the second dose calculation algorithm. Each of the algorithms can be iterated a plurality of times. The incremental dose calculation may use less precision, less accuracy, or otherwise proceed faster than the complete dose calculation algorithm in order to converge more quickly on an optimized plan. A first cutoff criterion may be applied to limit the number of iterations of the incremental dose calculation algorithm while a second, different, cutoff criterion is applied to limit the number of iterations of the complete dose calculation algorithm. The method of the present invention may be used for treatment plan comprising IMRT or arc treatment. The incremental dose calculation algorithm may be based on small changes to the results of the preceding dose calculation and limited to updating the results that were changed.

Another embodiment of the present invention comprises a method of optimizing a treatment plan for irradiating a treatment volume from a plurality of angles, including the steps of obtaining an initial dose calculation, thereafter, iteratively making dose calculations using a first algorithm until a first cut-off criterion is fulfilled and, thereafter, iteratively making dose calculations using a second algorithm until a second cut-off criterion is fulfilled, wherein the first and second cut-off criteria are different, and wherein the first and second dose calculation algorithms are different. According to the method of this embodiment each of the dose calculation algorithms are repeated a plurality of times. One of the algorithms may be a stochastic algorithm, such as a Monte Carlo algorithm, while the other is a deterministic algorithm. The algorithms may use different resolutions.

A treatment planning system according to an embodiment of the present invention may comprise a computing system having software stored on a tangible medium for optimizing a treatment plan for irradiating a treatment volume using a radiation therapy system, said radiation system being capable of irradiating said treatment volume from a plurality of angles, wherein the software includes a first dose calculation algorithm for iteratively performing substantially complete dose calculations until a first cutoff criterion is reached, based on input data comprising information about the treatment volume and further based on information about the capabilities of the radiation therapy system, and a second dose calculation algorithm for iteratively performing incremental dose calculations until a second cutoff criterion is reached. The treatment planning system software also include an algorithm for translating the results of an optimized treatment plan into instructions for operating the radiation therapy system by controlling the positioning of the leaves of a multileaf collimator and the angle of irradiation.

DETAILED DESCRIPTION

Figure 1A:
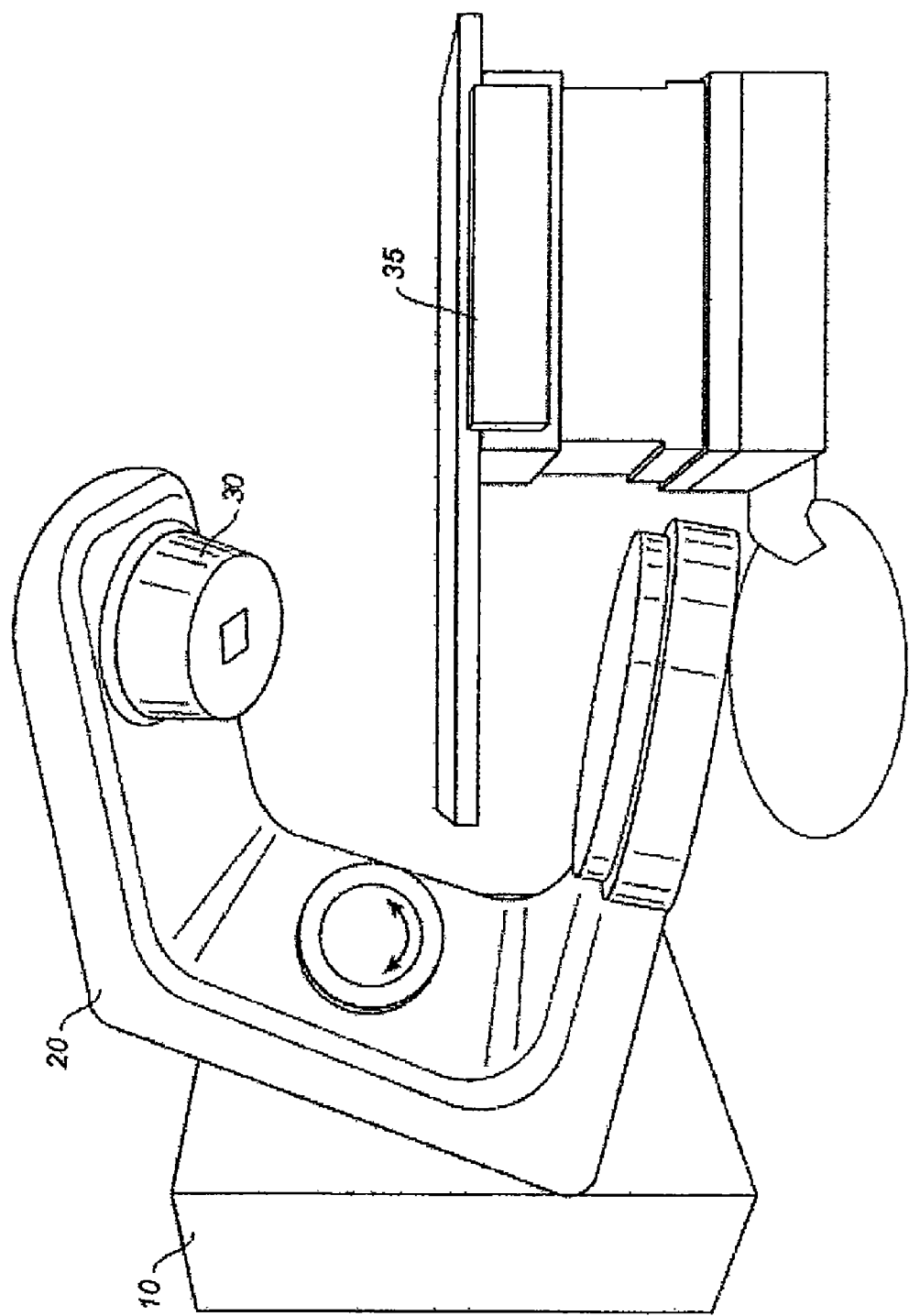
FIGS. 1A and 1B are perspective and side views of a radiation therapy system, as known in the prior art, of the type which may be used in connection with the present invention.
Figure 1B:
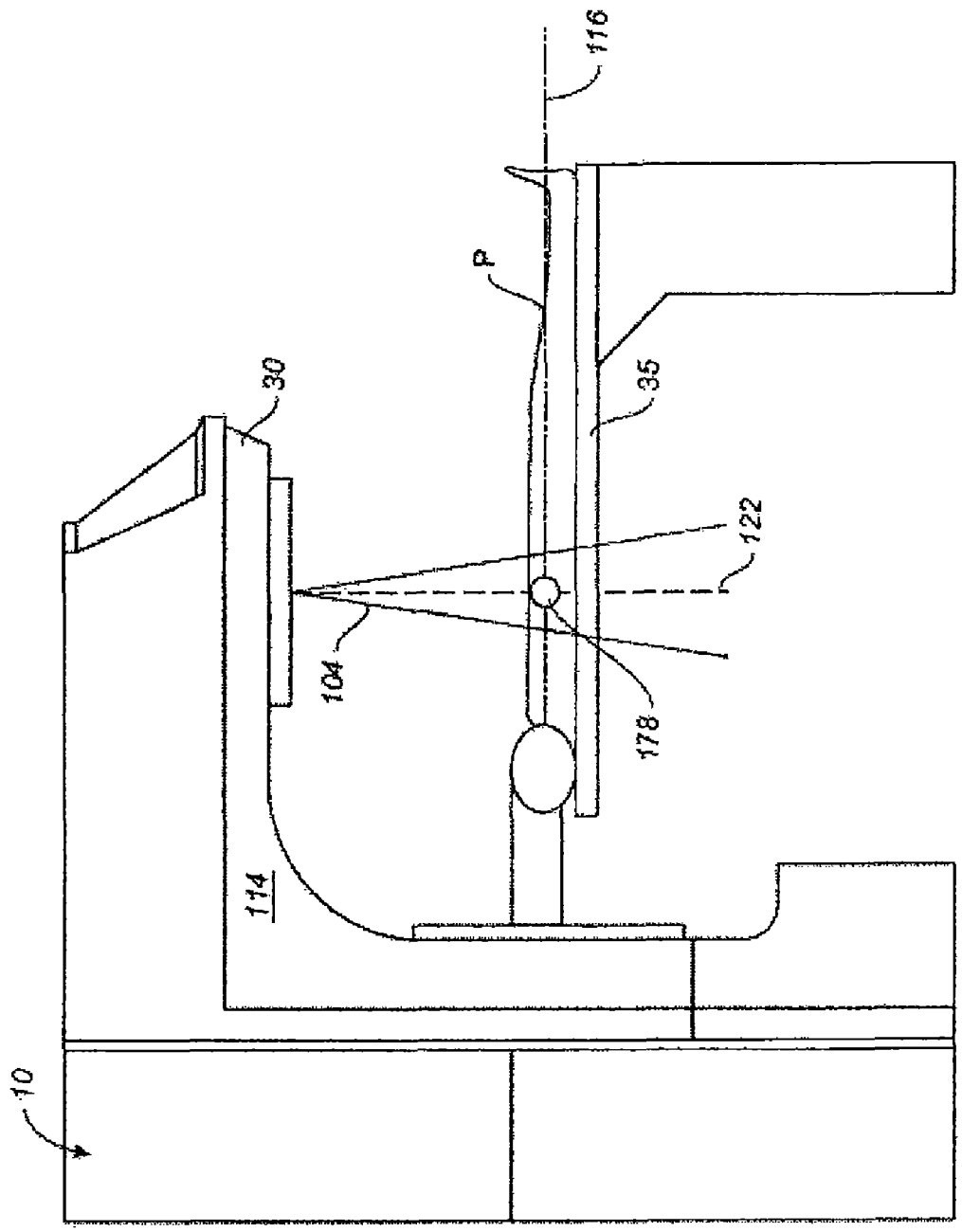

FIGS. 1A and 1B depicts a radiation therapy system of the type which may be used in connection with the present invention. Referring to FIG. 1A, a perspective view of radiation therapy system (in this case a linear accelerator) is shown. Typically, such a system is capable of generating either an electron (particle) beam or an x-ray (photon) beam for use in the radiotherapy treatment of patients on a treatment table 35. Other radiation therapy systems are capable of generating heavy ion particles such as protons. For purposes of the present discussion, only x-ray irradiation will be discussed. However, it will be appreciated by those skilled in the art that the same principles apply to other systems.

Stand 10 supports a rotatable gantry 20 with a treatment head 30. Next to stand 10 there is arranged a control unit (not shown) which includes operational electronics for controlling the different modes of operation of the accelerator. A high voltage source is provided within the stand or in the gantry, to supply voltage to an electron gun (not shown) positioned on an accelerator guide located in gantry 20. Electrons are emitted from the electron gun into the guide (not shown) where they are accelerated. A source supplies RF (microwave) power for the generation of an electromagnetic field within the waveguide. The electrons emitted from the electron gun are accelerated in the waveguide by the electromagnetic field, and exit the waveguide as a high energy electron beam, typically at megavoltage energies. The electron beam then strikes a suitable metal target, emitting high energy x-rays in the forward direction.

Referring now to FIG. 1B, a somewhat more detailed side view of a radiation therapy system of the type which may be used in connection with the present invention is shown. A patient P is shown lying on treatment table 35. X-rays formed as described above are emitted from the target in treatment head 30 in a divergent beam 104. Typically, a patient plane 116, which is perpendicular to the page in FIG. 1B, is positioned about one meter from the x-ray source or target, and the axis of gantry 20 is located on plane 116, such that the distance between the target and isocenter 178 remains constant when gantry 20 is rotated. Isocenter 178 is at the intersection between patient plane 116 and the central axis of beam 122. A treatment volume to be irradiated is located about the isocenter.

"Jaws" (not shown) or x-ray collimators comprising an x-ray blocking material, are positioned in head 30 to define the width of the x-ray beam at the patient plane. Typically, the jaws are moveable and, when fully open, define a maximum beam of about 40 cm×40 cm at patient plane 116. A multileaf collimator ("MLC") (not shown in FIG. 1B) is positioned at the exit of head 30, to further shape the x-ray beam. Since its introduction in 1990 the MLC has become a standard feature of most radiation therapy systems. Current MLCs sold by the assignee of the present invention use up to 120 individually controllable leaves, typically thin slices of tungsten, that can be moved into or out of the x-ray beam under the control of system software. The MLC can be used to collimate the x-rays to provide conformal treatment of tumors from various angles ("3D conformal,") as well as intensity modulated radiotherapy ("IMRT"), whereby different radiation doses are delivered to different portions of the treatment area. The treatment volume, i.e., the irradiated volume proximate to the isocenter in the path of the x-ray beam, is defined by the jaws, the angle of the head and the MLC. In IMRT the leaves of the MLC are moved, such that the treatment volume comprises the total volume exposed during the course of a treatment. In arc therapy, the gantry is moved while radiation is delivered.

Modern radiation therapy techniques involve the use of a treatment plan designed to irradiate a desired target volume, usually corresponding to a tumor, with a desired dose of x-rays (or other radiation). Most treatment planning involves the use of the MLC to provide conformal and/or intensity modulated irradiation. Generally speaking, a treatment plan comprises irradiating one or more selected portions of the treatment volume with a calculated dose of x-rays, and often involves irradiating a treatment area from a plurality of different angles or, in arc therapy, while the gantry is rotated. Various treatment planning software and other tools are available for developing specific treatment plans, and the details of the various techniques for creating such plans are known and will be described in further detail below. Again, generally speaking, after a treatment plan is created it is implemented, in part, by controlling the angle of incidence and the leaves of the MLC so as allow the desired radiation dose to reach the selected portions of the treatment volume from the selected angles or while the gantry is rotating. In the simplest type of treatment plan, the MLC is adjusted to provide static conformal irradiation of a specific site from a single angle. In more complex plans, the leaves are moved into different positions between or during irradiations. The leaves of the MLC can either be moved iteratively into different positions while the beam is off, with irradiation between movements, (such that the leaves are static during x-ray emission), or they can be continually moved during irradiation in a "sliding window" or other variable aperture technique. As noted above, an important aspect of the conformal and IMRT techniques that are associated with the use of MLCs is the ability to both provide a desired dose of radiation to a target volume while minimizing the dose delivered to adjacent healthy tissue.

As described in more detail in the Background section above, several techniques have been developed to create treatment plans for IMRT or conformal radiation therapy. Generally, these techniques are directed to solving the "inverse" problem of determining the optimal combination of angles, radiation doses and MLC leaf movements to deliver the desired total radiation dose to the target while minimizing irradiation of healthy tissue. This inverse problem is even more complex for developing arc therapy plans where the gantry is in motion while irradiating the target volume. Heretofore, radiation oncologists or other medical professionals, such as medical physicists and dosimetrists, have used one of the available algorithms to develop and optimize a treatment plan. Typically, such planning starts with volumetric information about the target tumor and about any nearby tissue structures. For example, such information may comprise a map of the planning target volume ("PTV"), such as a prostate tumor, which is prescribed by the physician to receive a certain prescribed therapeutic radiation dose with allowable tolerances. Volumetric information about nearby tissues may include for example, maps of the patient's bladder, spinal cord and rectum, each of which may be deemed an organ at risk and can only receive a much lower, maximum prescribed amount of radiation without risk of damage. This volumetric information along with the prescribed dose limits and similar objectives set by the medical professionals is the basis for calculating an optimized dose distribution and the treatment plan to deliver it. This may for example, be reduced to an objective function or a single figure of merit that accounts for the relative importance of various trade-offs inherent in such a plan along with constraints that must be met for the plan to be medically acceptable or physically possible. To create a deliverable treatment plan, treatment planning algorithms must account for the capabilities of the specific radiation therapy system they are used with. For example, the type, energy level and fluence of the radiation beam, and the capabilities of the MLC. Generally speaking, treatment planning algorithms proceed by calculating the radiation dose received by each voxel in the treatment volume, adjusting one or more variable system parameters, such as the angle of irradiation or the positions of the MLC leaves, and then recalculating the dose received by each voxel. This process is ideally performed iteratively until an optimized plan is reached. However, the amount of time needed to perform the large number of calculations for each iteration places a practical limit on the number of iterations that can be performed. Accordingly, the algorithm is terminated after a predetermined amount of time, after a predetermined number of iterations, or after some other practical limit is reached. Generally speaking, there is a trade-off between the accuracy and speed of the different algorithms available for treatment planning.

Figure 2:
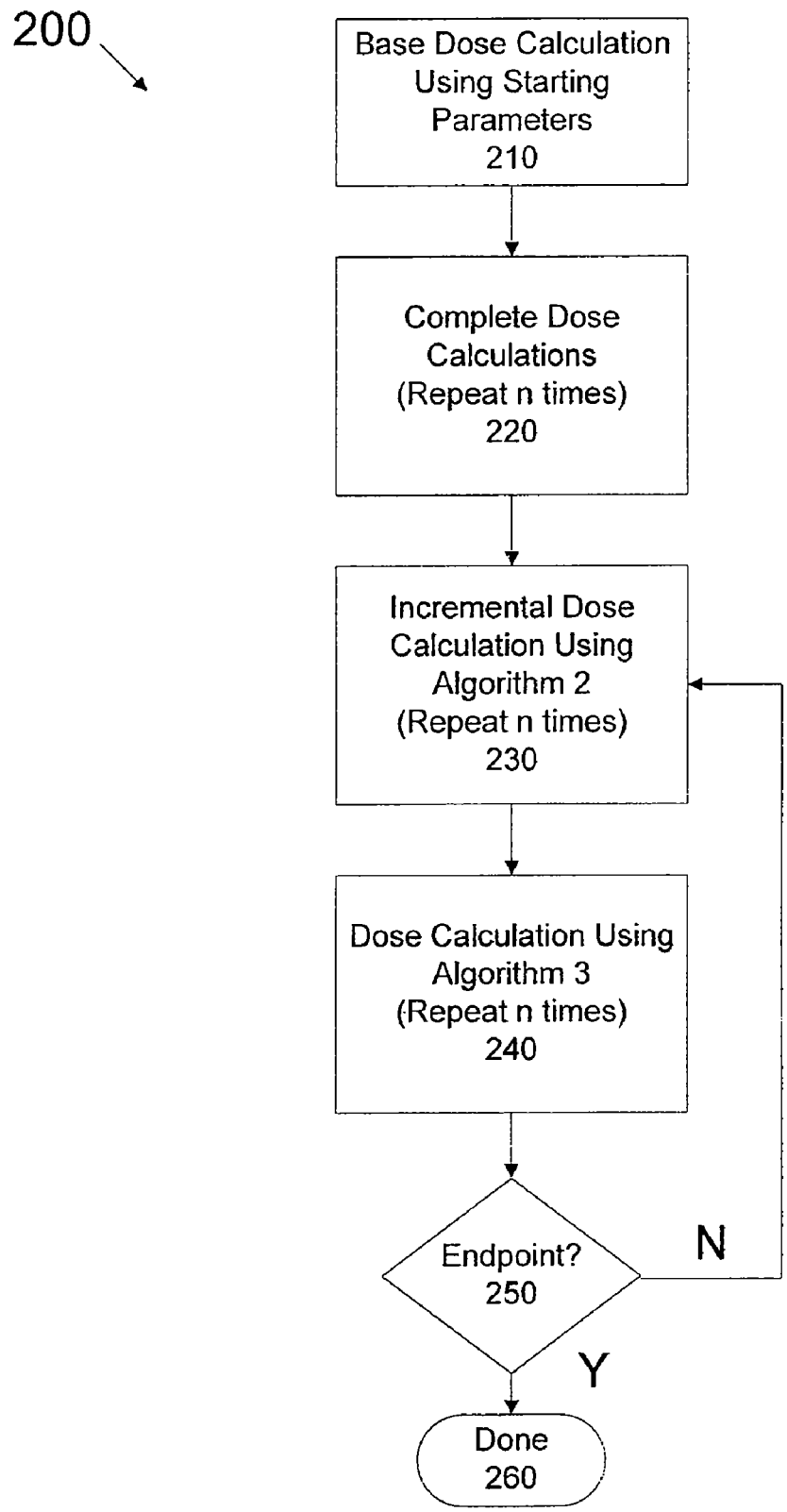
FIG. 2 is a flow chart in accordance with an embodiment of the present invention.

FIG. 2 is a flow chart 200 showing the steps of a general embodiment of the method of the present invention. The overall aim of the inventive method is to develop an optimized treatment plan for irradiating a treatment volume such that the target volume or tumor receives a prescribed dose of radiation, while limiting irradiation of adjacent healthy tissue to acceptable limits. The method starts with an initial or base dose calculation, at step 210, using starting parameters for developing the treatment plan. For purposes of the present invention, the manner of arriving at the starting parameters used in the base dose calculation is unimportant and so any of a variety of known methods for arriving at starting parameters is suitable. For example, the base calculation of step 210 may be based on parameters used in a prior radiotherapy for a similar tumor in a similar location. Thus, if the target tumor is in the prostate, many of the conditions that affect the treatment plan, such as the nature and type of nearby organs or other healthy tissue structures, may be very similar from one patient to the next. In such a case, the starting parameters for the treatment plan may be based on a typical plan for a typical patient (sometimes called a class solution or template) that is automatically adjusted in shape to better reflect the anatomy of the specific patient being treated. Alternatively, the starting parameters used in step 210 can be calculated from scratch based on information about the target and other structures in the treatment volume.

As noted above, typically radiation therapy proceeds over a period of time such that the dose to the target is fractionated into a number of treatment sessions. However, changes in the structures within the treatment volume require recalculation and reoptimization of the treatment plan between sessions. This may be done using the method of the present invention. In such a case, step 210 may simply use the optimized plan from the prior session. Alternatively the prior plan could for example be automatically adjusted in shape to better match the altered anatomy of the patient as presented as a starting point for reoptimization. Such an adjustment could for example utilize deformable registration.

Typically, the dose calculation of step 210 will not meet the treatment objectives and constraints established by the medical professional. Thus optimization typically is required which involves adjusting some of the parameters used in step 210 and performing a new dose calculation based on the adjusted parameters. In accordance with the present invention, a search algorithm selects a new set of parameters and a substantially complete dose calculation is then performed using any suitable algorithm at step 220. The dose calculation algorithm used at step 220 may be the same as the one used at step 210. For example, many optimization search algorithms, such as simulated annealing, proceed by changing the boundary conditions and using the new boundary conditions as parameters for performing a new dose calculation. Again, any suitable search algorithm known in the art may be used to adjust the parameters for the dose calculation of step 220.

In accordance with known prior art techniques, step 220 would simply be repeated multiple times until reaching an end point or cut-off, e.g., ideally until the optimization finds a global minimum in a relevant objective function or figure of merit, or otherwise until a predetermined amount of time has elapsed, or a predetermined number of iterations is performed. In contrast, as described below, the method of the present invention does not use the same algorithm from start to finish. Nonetheless, the calculation of step 220 may be repeated a number of times before moving to step 230.

Next, at step 230, an incremental dose calculation is performed in accordance with the present invention. Incremental dose calculations of step 230 are preferably performed a number of times before moving to step 240. In contrast to known prior art techniques, the present invention uses a different dose calculation algorithm to perform the incremental dose calculations of step 230. In accordance with the present invention, a different algorithm is used for the incremental dose calculation of step 230 in order to achieve one or more of the following: (1) faster calculation time to speed convergence towards an objective, (2) greater accuracy once convergence is approached, or (3) to overcome some other limitation of the base algorithm of step 220.

In specific embodiments of the present invention, the incremental dose calculation of step 230 may have various features or aspects. For example, the incremental dose calculations of step 230 can be limited in scope, e.g., focusing only updating specific changes suggested by the optimization search algorithm or on specific sub-volumes within the overall treatment volume such as the target, etc. Likewise, the incremental dose calculations of step 230 may simply use a different technique to overcome a shortcoming of the base calculation used at step 220. For example, the base or complete dose calculation of step 220 may be a stochastic technique such as Monte Carlo, while the incremental dose calculations of step 230 may be performed using a faster deterministic technique such as an additive kernel summation. When alternating between calculation techniques, different criteria may be employed. For example, the difference produced by using the different dose calculation methods can be estimated.

In another embodiment, the base and incremental dose calculations of steps 220 and 230 can be different deterministic techniques. For example, AAA or CCC can be used for the base calculation of step 220 and PBC for the incremental calculations of step 230. In another embodiment, the same basic techniques can be used at steps 220 and 230 but with different cut-off range, resolution, or precision. For example a pencil beam algorithm can be applied to both the base dose calculation and incremental dose calculation. Thus, different kernel sizes can be used in the two steps, with larger (lower resolution/less accurate) kernel size for the incremental calculations to reduce computation time. Likewise, the techniques used for the incremental calculations can be performed with less numerical precision such that they can be performed more quickly.

As noted, the incremental dose calculations of step 230, like the base calculations of step 220, are preferably repeated a number ("n") times, where n may be one. In each instance, the value of n can be predetermined or can be based on another parameter. Thus, for example, the incremental dose calculation step of 230 can be repeated until a time out is reached, or until some other criterion is met, in which case the value of n may not be known at the outset of step 230.

The incremental dose calculations of the present invention may be used accelerate the optimization process by focusing on one aspect of the problem. Thus, for example, in one pass, the incremental dose calculations of step 230 may focus on a specific gantry angle, i.e., one beam direction.

After completing the incremental dose calculation of step 230, the treatment planning method of the present invention then proceeds to perform another complete dose calculation as indicated at step 240 of FIG. 2. In one embodiment, "Algorithm 3" of step 240 is the same as "Algorithm 1" at step 220, such that the dose calculation technique iteratively repeats steps 220 and 230. In another embodiment, different techniques for are used for the complete dose calculations of steps 220 and 240. Whether they are the same or not, different cut-off criteria may be used for each of the complete dose calculations of steps 220 and 240, as well as the incremental dose calculations of step 230.

After performing the complete dose calculation of step 240, a determination is made at step 250 whether the process has reached an endpoint or final cutoff. If the final endpoint has been reached the process is completed, as indicated at step 260. If not, another set of incremental dose calculations (step 230) are performed, followed by one or more complete dose calculations (step 240), and so on until the endpoint is reached. While both steps 230 and 240 are repeated iteratively, it is contemplated that a greater number of incremental calculations will be performed than complete calculations. Again, endpoint 250 may be based on elapsed time or any other suitable criterion. The desired endpoint is based on reaching convergence on a global minimum in an objective function or figure of merit while also meeting the constraints established at the outset of optimization.

In yet another embodiment, different incremental dose calculation techniques are used at different stages of the optimization process or between complete dose calculations. For example, as the process converges on an optimal solution, different incremental algorithms may offer different advantages. For example, between complete dose calculations incremental dose calculations may start with a less accurate dose calculation algorithm and then calculate the incremental changes with more accurate dose calculation algorithm (starting from previous accurate dose calculation and calculate only changes).

It will be understood that each of the dose calculations, whether complete or incremental, will have or will provide the basis for calculating an associated set of machine parameters, such as gantry angles, MLC movements, arc movements, irradiation times, etc., such that at the end of the process the linear accelerator, or other treatment system, can be controlled to implement the optimized plan. Methods for taking a treatment plan and using it to control machine movements are known in the art, and will not be described in detail. The Eclipse™ treatment planning software referenced above can be used for this purpose. In some instances, after the treatment plan optimization process is completed, the treatment planning software will then perform a final complete dose calculation using a more accurate but slower algorithm. In view of this, it is not necessary for the final step of the optimization process to be a complete dose calculation. Instead, optimization process could end with an incremental calculation.

Figure 3:
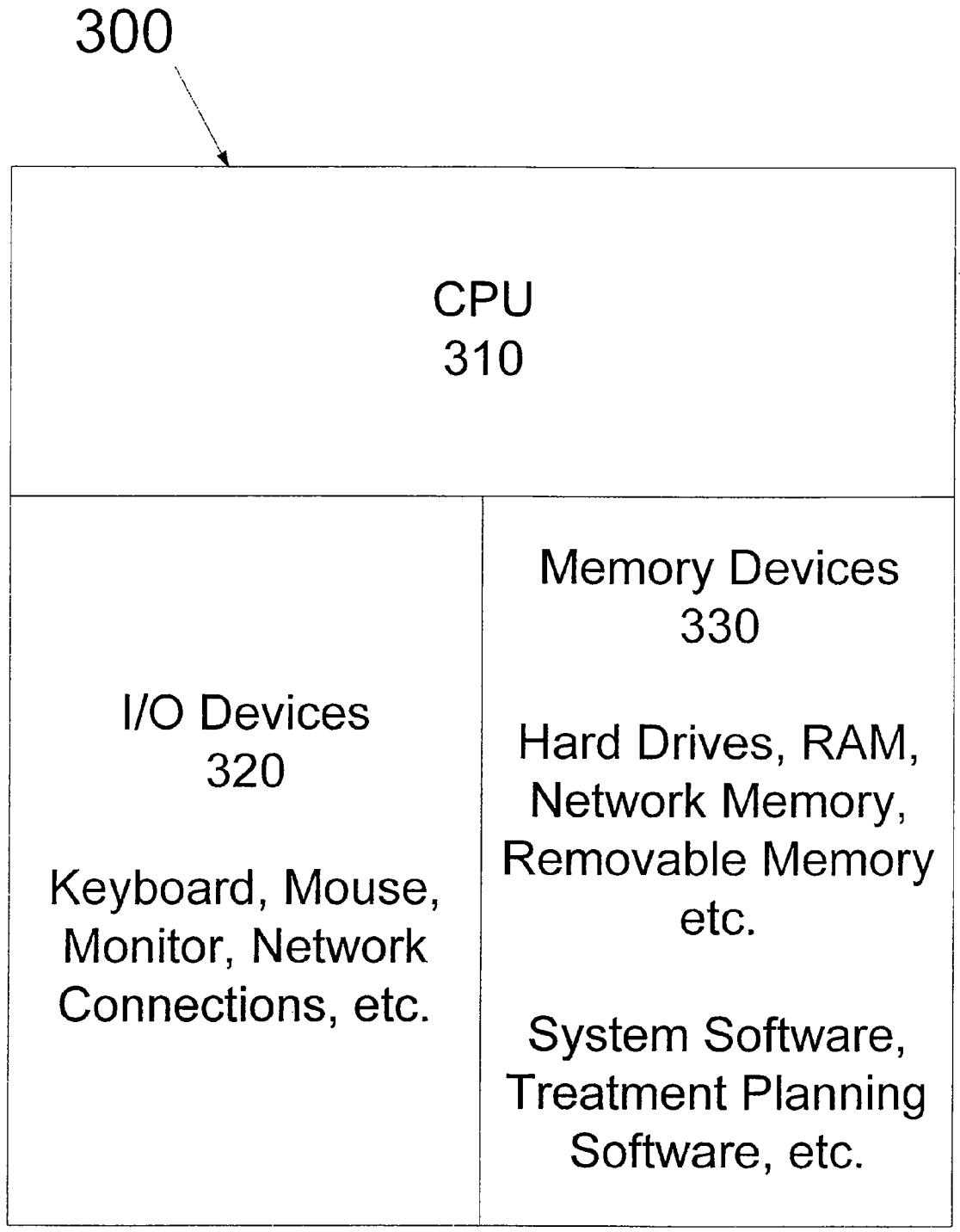
FIG. 3 is a block diagram of a treatment planning system in accordance with the present invention.

FIG. 3 represents a treatment planning system 300 in accordance with the present invention. Treatment planning system 300 comprises a computer system having a central processing unit (CPU) 310 bidirectionally connected to various I/O devices 320, such as one or more keyboards, pointing devices, monitors, network connections, etc., and bidirectionally connected to various memory devices 330, such as one or more hard disks, random access memory, flash memory and/or remote memory devices accessed over a local or wide area computer network. In some instances memory devices are considered to be I/O devices. However, for convenience they are treated separately herein. Memory devices 330 comprise one or more tangible media for storing various system software programs. Collectively, CPU 310, I/O devices 320 and memory devices 330 constitute a computing system, which may additionally include other conventional elements typically found in computing systems.

According to the present invention, I/O devices 320 include one or more data input devices for entering and patient data, for example, information about the tumor to be treated and about adjacent tissue structure, the prescribed dose to applied to the tumor, and the maximum radiation dose that can be tolerated by adjacent organs. Such patient data may comprise images from CT or MRI scans showing such structures. In one embodiment, I/O devices 320 comprise hardware and/or software tools to allow the system operator to digitize boundary and other information about such structures for use in treatment planning.

Software stored in memory devices 330 is loaded and processed in the computer system in any conventional manner. In accordance with the present invention, the software stored in memory devices 330 comprises software for optimizing a treatment plan for irradiating a target volume using a radiation therapy system having a multileaf collimator and capable of irradiating a treatment volume from a plurality of angles. The treatment planning software includes at least one dose calculation algorithm for performing substantially complete dose calculations based on input data comprising information about the treatment volume and further based on information about the capabilities of the radiation therapy system, and at least one dose calculation algorithm for iteratively performing incremental dose calculations. As indicated above in connection with FIG. 2, the software iteratively repeats complete and incremental dose calculations until interim and final cut-off criteria are reached, in order optimize the treatment plan.

In a preferred embodiment the treatment planning system software further comprises an algorithm for translating the results of an optimized treatment plan into instructions for operating the radiation therapy system by controlling the positioning of the leaves of the multileaf collimator and the angle of irradiation. Treatment planning system can either be directly connected to system computer which controls the radiation system, the control instructions can be downloaded into the radiation system controller via a local or wide area network connection, or in any other known manner.

The embodiments described above are illustrative of the present invention and are not intended to limit the scope of the invention to the particular embodiments described. Accordingly, while one or more embodiments of the invention have been illustrated and described, it will be appreciated that various changes can be made therein without departing from the spirit or essential characteristics thereof. Accordingly, the disclosures and descriptions herein are not intended to be limiting of the scope of the invention, which is set forth in the following claims.

What is claimed is:

1. A method of optimizing a treatment plan for irradiating a treatment volume within a patient from a plurality of angles, comprising:

(a) making with a computing system a substantially complete dose calculation using a first dose calculation algorithm, and (b) thereafter, making with the computing system at least one incremental dose calculation using a second dose calculation algorithm that is different from said first dose calculation algorithm.

2. The method of claim 1 further comprising:

(c) making a substantially complete dose calculation after step (b) using a third dose calculation algorithm that is different from said second dose calculation algorithm.

3. The method of claim 2 wherein steps (b) and (c) are each iterated a plurality of times.

4. The method of claim 3 wherein a first cutoff criterion is applied to limit the number of iterations of step (b) and a second cutoff criterion is applied to limit the number of iterations of step (c), and wherein said first and second cutoff criteria are different.

5. The method of claim 2 wherein step (b) is performed a plurality of times before proceeding to step (c).

6. The method of claim 2 wherein the algorithms used for the substantially complete dose calculations of steps (a) and (c) are the same.

7. The method of claim 1 wherein said incremental dose calculation is performed with less precision than said substantially complete dose calculation.

8. The method of claim 1 wherein said incremental dose calculation is performed with less accuracy than said substantially complete dose calculation.

9. The method of claim 1 wherein said incremental dose calculation algorithm is faster than said complete dose calculation algorithm.

10. The method of claim 9 wherein said incremental dose calculation is based on a small change to the results of the preceding dose calculation and is limited to updating the results that were changed.

11. The method of claim 1 wherein said treatment plan comprises IMRT.

12. The method of claim 1 wherein said treatment plan comprises arc treatment.

13. A method of optimizing a treatment plan for irradiating a treatment volume within a patient from a plurality of angles, comprising:

(a) obtaining with a computing system an initial dose calculation, (b) thereafter, iteratively making with the computing system dose calculations using a first algorithm until a first cut-off criterion is fulfilled, and (c) thereafter, iteratively making with the computing system dose calculations using a second algorithm until a second cut-off criterion is fulfilled, wherein said first and second cut-off criteria are different, and wherein said first and second dose calculation algorithms are different.

14. The method of claim 13 wherein steps (b) and (c) are each repeated a plurality of times.

15. The method of claim 13 wherein steps (a) and (b) are performed using different resolutions.

16. A method of optimizing a treatment plan for irradiating a treatment volume within a patient from a plurality of angles, comprising:

(a) obtaining with a computing system an initial dose calculation, (b) thereafter, iteratively making with the computing system dose calculations using a first algorithm until a first cut-off criterion is fulfilled, and (c) thereafter, iteratively making with the computing system dose calculations using a second algorithm until a second cut-off criterion is fulfilled, wherein said first and second cut-off criteria are different, wherein said first and second dose calculation algorithms are different, wherein one of steps (b) or (c) is a stochastic algorithm and the other is a deterministic algorithm.

17. The method of claim 16 wherein said stochastic algorithm is a Monte Carlo algorithm.

18. A treatment planning system comprising a computing system having software stored on a tangible medium for optimizing a treatment plan for irradiating a treatment volume using a radiation therapy system, said radiation system being capable of irradiating said treatment volume from a plurality of angles, said software comprising:
   a first dose calculation algorithm for iteratively performing substantially complete dose calculations until a first cut-off criterion is reached, based on input data comprising information about the treatment volume and further based on information about the capabilities of the radiation therapy system,
   a second dose calculation algorithm for iteratively performing incremental dose calculations until a second cutoff criterion is reached.

19. The treatment planning system of claim 18, wherein said software further comprises an algorithm for translating the results of an optimized treatment plan into instructions for operating the radiation therapy system by controlling the positioning of the leaves of a multileaf collimator and the angle of irradiation.

20. A non-transitory tangible computer-readable storage medium having treatment planning software stored thereon, the treatment planning software for optimizing a treatment plan for irradiating a treatment volume using a radiation therapy system, said radiation system being capable of irradiating said treatment volume from a plurality of angles, said software comprising:
   (a) instructions for causing the radiation system to make a substantially complete dose calculation using a first dose calculation algorithm, and
   (b) instructions for causing the radiation system to, thereafter, make at least one incremental dose calculation using a second dose calculation algorithm that is different from said first dose calculation algorithm.

* * * * *